United States Patent [19]

Parlow

[11] 4,010,256
[45] Mar. 1, 1977

[54] MALE CONTRACEPTIVE AND METHOD OF ACHIEVING MALE CONTRACEPTION

[75] Inventor: Albert F. Parlow, Torrance, Calif.

[73] Assignee: Professional Staff Association of the Los Angeles County Harbor General Hospital, Torrance, Calif.

[22] Filed: July 30, 1975

[21] Appl. No.: 600,301

[52] U.S. Cl. .............................. 424/88; 260/42 R; 424/177

[51] Int. Cl.² ................ A61K 37/38; A61K 39/00

[58] Field of Search .......... 424/177, 88; 260/112 R

[56] References Cited

OTHER PUBLICATIONS

Steinberger et al., "Recent Progress in Hormone Research," vol. 26, pp. 547–548, (1970).
Steelman et al., "Recent Progress in Hormone Research," vol. 15, pp. 115–125, (1959).

Primary Examiner—Lewis Gotts
Assistant Examiner—Dolph H. Torrence
Attorney, Agent, or Firm—I. Morley Drucker

[57] ABSTRACT

A method of immunization of human males to achieve contraception is provided which includes the step of administering, periodically, predetermined amounts of, non-primate, highly purified FSH having a biologic potency of at least 1,000 I.U. (International Units)/mg, an LH contamination of below 11 I.U./mg and a TSH contamination of less than 0.1 I.U./mg, to a human male until his sperm production declines below about twenty million per cc. FSH is the Follicle Stimulating Hormone; LH the Luteinizing Hormone; and TSH the Thyroid Stimulating Hormone.

5 Claims, No Drawings

MALE CONTRACEPTIVE AND METHOD OF ACHIEVING MALE CONTRACEPTION

SUMMARY OF THE INVENTION

Extensive laboratory and clinical data indicate that FSH is the primary agent in stimulating and regulating sperm production, but FSH does not affect secretion of the male sex hormone, testosterone. Therefore, active immunization of normal human males with sheep or rat FSH will result in formation of antibodies which will neutralize the subjects endogenous FSH secretion, such that the subject's sperm production will decline and infertility or contraception will result. Androgen production and potency will be unaffected. With occasional "booster" immunizations, the effect can be maintained permanently. Without "booster" immunizations, the effect will "wear off."

Highly purified FSH will be administered as an "alum precipitated"* antigen in a dose of 0.5 mg. three times monthly to normal human males, until suitably high titers of antibodies are generated, i.e. until sperm production declines below 20 million per cc.

*The procedure for preparation of "alum precipitated" antigen is described in "Methods in Immunology and Immunochemistry" - Ch. 2 pp. 197–209 (Academic Press, N.Y. 1967) Antibody formation can be monitored by suitable radio immunoassay techniques. Sperm counts will be accomplished by standard methods of semen analysis.

The use of highly purified FSH, as opposed to the crude extracts utilized in the 1950's, will maximize the likelihood of achieving high antibody titers with minimal side reactions, if any. The highly purified FSH is essentially devoid of luteinizing hormone (LH) activity, unlike the crude extracts previously used, such that antibodies will be generated only to FSH, not to LH as well. In addition, the use of "alum precipitated antigen" preparations of FSH will again maximize the likelihood of high antibody titer formation, which is essential to success of the procedure.

DESCRIPTION OF PREFERRED EMBODIMENT

The procedure for isolation and purification of Follicle Stimulating Hormone (FSH) from sheep or rat pituitary glands is as follows:

1. Collection of Pituitaries

The pituitaries derived from sheep or rats should be removed at the time of autopsy and placed directly into pure acetone without exposure to any other fixative. The pituitaries may be stored (in the cold) for many months in acetone, the volume of acetone being at least 20 times the volume of the glands. It is recommended that acetone be poured off occasionally and fresh acetone added to the glands. Before shipping the acetone should be poured off, glands rinsed with fresh acetone and sent in a well-sealed container.

2. Preparation of Acetone Dried Powder

On arrival the glands are resuspended in fresh acetone and stored in the cold until enough glands are collected. Each gland is then peeled to separate connective tissues and small pieces of bones. The glands are minced with fresh acetone in an electric meat grinder (Homo-mixture, Hudson, N.Y.). The mixture filtered on a Buchner funnel layered with a Whatman No. 1 paper, washed with more acetone and dried in a desiccator under water pump vacuum. The dried mixture is then put through a Wiley cutting mill to make powder.

3. Extraction of Gonadotropins (Glycoproteins)

The glycoproteins are extracted with a mixture of 600 ml. of 10% (v/v) ammonium acetate adjusted to pH 5.1 and 400 ml. of 96% (v/v) rthanol. All the operations are done at 4°.

To 100 grams of pituitary powder is added 1700 ml. of cold solvent mixture and the mixture is stirred for 2 nights in the cold. This is either centrifuged or filtered and the filter cake is washed with 300 ml. of the solvent. Glycoproteins are precipitated from this combined extract by adding 2 volumes of cold 96% ethanol slowly stirring.

The stirring is continued for another 30 minutes and the mixture is left at 4° for 2 days to complete precipitation. By this time all the precipitate is collected at the bottom of the jar. Most of the supernate is siphoned off and the precipitate is recovered by centrifugertion. The precipitate is washed once with cold 96% ethanol, twice with cold ether and dried in vacuo.

The pituitary residue is mixed with cold acetone and washed thoroughly on a Buchner funnel with about 5 liters of acetone. The filter cake is either spread out on a tray for air drying or dried in a desiccator under water pump vacuum.

The FSH in the precipitate was purified further by chromatography on a column of carboxymethyl-cellulose (Whatman CM-1). For example, 25 grams of the precipitate was solubilized in 0.005M ammonium acetate buffer, pH 5.5, and applied to a 9.7 cm. by 94 cm. column of CM-cellulose. All of the FSH was unabsorbed to this column and collected in a fraction collector. The eluate was dialyzed and brought to dryness by lyophilization.

Thereafter, this FSH fraction was purified further by column chromatography on diethylaminoethyl-cellulose (Whatman DE-1). For example, 2 grams of the FSH fraction was solubilized in 0.005 potassium phosphate buffer at pH 7.0 and applied to a 4 cm. by 25 cm. column of diethylaminoethyl-cellulose. After elution of the unadsorbed material, the FSH was eluted with 0.06 molar potassium phosphate at pH 7.0. Again, the eluate fraction containing FSH was dialyzed and brought to dryness by lyophilization.

Final purification of the FSH was accomplished by column chromatography on Sephadex G-100 (Pharmacia) in 0.05M ammonium bicarbonate buffer. The FSH-containing fraction was brought to dryness by lyophilization.

At each step the FSH activity was detected and evaluated by means of a biological assay (the hCG- augmentation bioassay).

The final product derived from sheep pituitary glands has a biologic potency of 1000 I.U./mg. or greater. Its contamination with other pituitary glycoprotein hormones was quite low. Thus, the luteinizing hormone (LH) contamination was below 11 I.U./mg. (as measured by the Parlow, ovarian ascorbic acid depletion bioassay) and its contamination with thyroid stimulating hormone (TSH) was less than 0.1 I.U. (as measured by the McKenzie mouse bioassay).

The final product derived from rat pituitary glands has a biologic potency of at least 3750 I.U./mg., the LH and TSH contamination being below 11 I.U./mg. and 0.1 I.U./mg. respectively.

The highly purified FSH is administered intramuscularly as an "alum precipitated antigen" in a dose of 0.5 mg. three times monthly to normal human males, until suitably high titers of antibodies are generated, i.e. until sperm production declines below 20 million per cc. Antibody formation can be monitored by suitable radioimmunoassay techniques. Sperm counts will be accomplished by standard methods of semen analysis.

I claim:

1. A method of immunization of human males to achieve contraception which includes the step of administering, periodically, predetermined amounts of, non-primate, highly purified FSH having a biologic potency of at least 1,000 I.U./mg., an LH contamination of below 11 I.U./mg. and a TSH contamination of less than 0.1 I.U./mg. to a human male until his sperm production declines below about twenty million per cc.

2. The method of claim 1 wherein said non-primate highly purified FSH is administered intramuscularly to the patient in an alum precipitate.

3. The method of claim 1 wherein said highly purified FSH is derived from sheep pituitary glands.

4. The method of claim 1 wherein said highly purified FSH is derived from rat pituitary glands having a biologic potency of at least 3750 I.U./mg.

5. A contraceptive preparation for the reduction of sperm production which consists essentially of:
a predetermined quantity of a non-primate, highly purified FSH having a biologic potency of at least 1,000 I.U/mg., an LH contamination of below 11 I.U/mg. and a TSH contamination of less than 0.1 I.U/mg.

* * * * *